US006071261A

United States Patent [19]

Augusto

[11] Patent Number: 6,071,261

[45] Date of Patent: Jun. 6, 2000

[54] METHOD AND APPARATUS FOR ORALLY ADMINISTERING A LIQUID, MEDICATION, OR A SUSPENSION TO A PATIENT

[76] Inventor: Jose F. Augusto, 32 Greencliff Dr., Niantic, Conn. 06357

[21] Appl. No.: 09/015,580

[22] Filed: Jan. 29, 1998

[51] Int. Cl.[7] .................................................. A61M 1/00

[52] U.S. Cl. .............................. 604/73; 604/77; 606/234; 606/236

[58] Field of Search ................................. 604/73, 77, 79, 604/245, 246, 248, 249; 606/234, 236

[56] References Cited

U.S. PATENT DOCUMENTS 3,426,755 2/1969 Clegg ........................................ 604/77
3,572,337 3/1971 Schunk ...................................... 604/77

*Primary Examiner*—John D. Yasko
*Attorney, Agent, or Firm*—McCormick, Paulding & Huber LLP

[57] ABSTRACT

In an apparatus for orally administering a dosage of a liquid, medication, or a suspension, to patients able to swallow but otherwise unable to independently ingest the liquid medication, or suspension, a sleeve is provided and includes a first open end and a closed second end. The sleeve defines an reservoir or reservoir, and a flange having an aperture extending therethrough and in communication with the reservoir extending outwardly from the second end. A hollow tube is attached to the flange and is adapted to be inserted into a patient's mouth to a point where the end of the tube is adjacent to the patient's throat. A plunger having an end adapted to slide and to seal against an interior wall of the reservoir is included and can move between a first and a second position to draw the liquid, medication, or suspension into the reservoir and inject it into the patient's mouth.

8 Claims, 1 Drawing Sheet

METHOD AND APPARATUS FOR ORALLY ADMINISTERING A LIQUID, MEDICATION, OR A SUSPENSION TO A PATIENT

FIELD OF THE INVENTION

The present invention relates generally to medical devices, and more particularly to a method and apparatus whereby a dosage of a liquid, medication, or suspension can be administered to a patient able to swallow, but otherwise unable to independently ingest the liquid, medication, or suspension.

BACKGROUND OF THE INVENTION

The present invention is directed to a method and apparatus for administering liquids and suspensions to a patient able to swallow but otherwise unable to independently ingest the liquid, medication or suspension, and will be described herein as applied to such use. As used herein, the term "patient" should be broadly construed to include human as well as veterinary patients.

In addition, the term "suspension" should be broadly construed to encompass both mixtures of two or more medications, or a medication and a liquid, where one of the constituents is in a powder or other solid form, as well as nutritional supplements, such as but not limited to purees of different foods.

For a variety of different reasons, oral administration of liquids or suspensions to patients can sometimes be difficult. For example, when attempting to orally administer a dose of liquid medicine to a child the usual method is to employ a spoon, either of a type specific to a certain measure, or a standard household spoon. However, if the child refuses to take the medication, it is difficult to administer it without some loss. Where medication is spilled as a result of attempting to administer it to an uncooperative child, more is often given to compensate for the amount lost. This sometimes results in over-medicating the child. The same difficulty is encountered when attempting to administer liquids, medications, or other suspensions to veterinary patients.

In addition to the difficulties associated with the oral administration of liquids or suspensions to juvenile and veterinary patients, the problem sometimes occurs where a patient is able to swallow, but otherwise cannot autonomously ingest the liquid, medication or suspension. This is particularly true with patient suffering from varying degrees of paralysis in the mouth and jaw area resulting from a stroke or other affliction. In these instances the use of a spoon or cup can be ineffective because the patient is unable to move the muscles necessary to transport the administered liquid, medication or suspension from the lips to the throat where it can be swallowed. While medications can be administered via injection or intravenously, a feeding tube is often necessary to provide nutrients to the patient. This results in discomfort to patients who would otherwise be able to swallow the liquids, medication or suspensions if the point of delivery was moved adjacent to the patient's throat.

Based on the foregoing, it is the general object of the present invention to provide a device for orally administering liquids, medications, or suspensions to patients, that overcomes the above-described problems and drawbacks of prior art devices.

It is a more specific object of the present invention to provide a device that places the point of delivery of the liquids, medications, or suspensions adjacent to the patient's throat.

SUMMARY OF THE INVENTION

The present invention is directed to an apparatus for orally administering a dosage of a liquid, a suspension, or medication to patients able to swallow but otherwise unable to independently ingest the liquid, medication, or suspension. The apparatus includes a sleeve that has a first open end and an interior area or reservoir for retaining the liquid, medication, or suspension, defined by an interior wall surface and a closed end. A flange depends outwardly from the closed end and defines an aperture extending therethrough and in communication with the reservoir.

The apparatus also includes a manually operable plunger that has a stem portion, and an end adapted to slidingly and sealingly engage the interior wall surface. The plunger is movable between a first position wherein the end is adjacent to the first end of the sleeve, and a second position wherein the end is adjacent to the second end of the sleeve for drawing the liquid, medication, or suspension into, and expelling it from the reservoir.

In the preferred embodiment of the present invention, an elongated hollow tube is also provided and has a first end coupled to the flange and a second end adapted to be positioned at a point within a patient's mouth adjacent to the patient's throat. In operation, the second end of the tube is positioned in a receptacle containing the liquid, medication or suspension and the plunger is manually moved from the second to the first position, drawing the liquid, medication or suspension into the reservoir. Subsequently, the tube is positioned in the patient's mouth and the end of the plunger is moved from the first to the second position, such that the liquid, medication, or suspension contained within the reservoir is injected out of the second end of the tube into the patient's mouth, adjacent to the patient's throat where it is readily swallowed by the patient.

In an embodiment of the present invention, a valve is interposed between, and coupled at one end to the flange and at an opposite end to the hollow tube. The valve is manually operable between a closed position wherein the liquid, medication, or suspension retained in the reservoir, is prevented from leaking out of the tube, and an open position wherein the liquid, medication, or suspension can be injected through the tube and into the patient's mouth.

Instead of a valve, a stopcock can be coupled between the sleeve and the hollow tube and is adapted to be coupled to at least two sleeves. The stopcock includes means for selectively allowing the contents of one reservoir in one sleeve to be injected through the hollow tube, while preventing the contents from the other sleeve from intermingling with the contents in the first sleeve. Accordingly, the apparatus of this embodiment of the present invention can be configured so that the patient can receive nutrients in the form of a liquid or suspension from the reservoir of one sleeve, and medication from the reservoir of another sleeve.

In addition to the foregoing, the hollow tube can be flexible, or semi-flexible. Where a semi-flexible tube is employed, the rigidity or stiffness of the tube is such that it can be bent to conform to a desired shape and will retain that shape. For example, in patient's that are unable to open their mouths, the semi-flexible tube can be bent to conform to the shape of the passage between the patient's teeth and cheek. This will allow the end of the tube to be easily positioned in close proximity to the patient's throat, thereby insuring that the patient will not have difficulty swallowing.

DETAILED DESCRIPTION OF THE PREFERRED EMBODIMENTS

Figures 1, 2, 3:
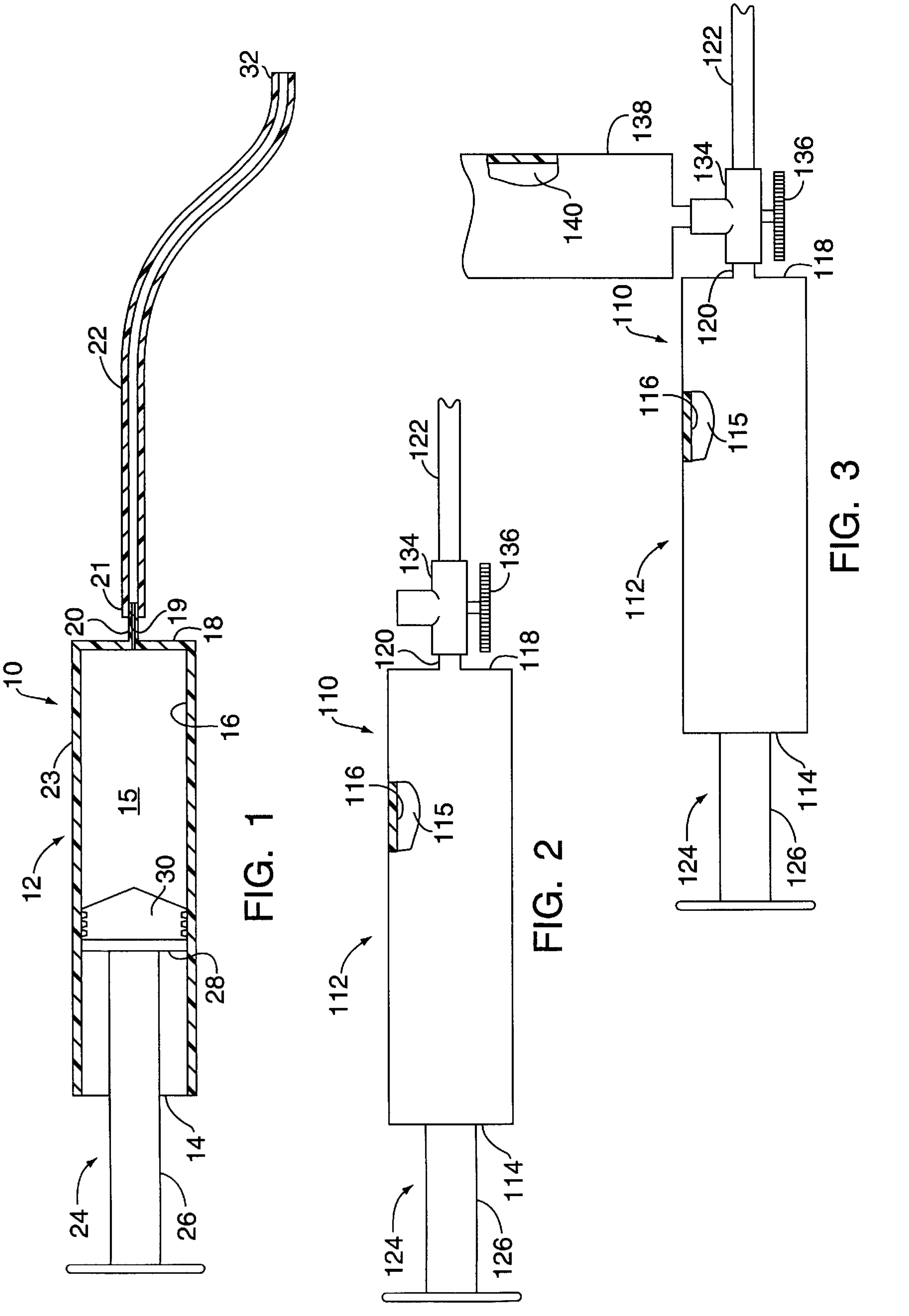
FIG. 1 is a cross-sectional, front elevational view of an apparatus embodying the present invention.
FIG. 2 is a partial front elevational view of an alternate embodiment of the apparatus of the present invention showing a stopcock positioned between the sleeve and the hollow tube of the apparatus of FIG. 1.
FIG. 3 is a partial front elevational view of the embodiment of FIG. 2 showing a pair of sleeves coupled to the stopcock.

An apparatus for orally administering a dosage of a liquid, a suspension, or medication to patients able to swallow, but otherwise unable to independently ingest the liquid, medication, or suspension, is shown in FIG. 1 and generally designated by the reference numeral 10. The apparatus 10 includes a sleeve 12 having a first open end 14, and an interior area or reservoir 15 defined by an interior sleeve wall 16, and a closed second end 18, for retaining the dosage of liquid, medication, or suspension. The closed second end 18 includes an outwardly depending flange 20 having an aperture 22 extending therethrough and in fluid communication with the reservoir 15. An elongated flexible hollow tube 22 is coupled to the flange 20 at a first end 21. The sleeve 12 can also include a transparent portion (not shown) through which the contents of the reservoir 14 can be viewed. In addition, indicia (not shown) can be defined by an external surface 23 of the sleeve 12 to provide an indication of the amount of liquid medication, or suspension that is contained in the reservoir 15.

The apparatus also includes a manually operable plunger 24 having a stem portion 26 and an end 28 adapted be received in, and to slidingly and sealingly engage the interior sleeve wall 16. The plunger 24 is movable between a first position wherein the end 28 is adjacent to the closed second end 18 of the sleeve 12, and a second position, wherein the end 28 is adjacent to the open first end 14 of the sleeve. In the preferred embodiment of the present invention, the sleeve 12 is cylindrical and an elastomeric tip 30 is attached to the end 28 of the plunger 24. The elastomeric tip 30 extends transversely across the diameter defined by the reservoir 14 and circumferentially engages the interior sleeve wall 16. While an elastomeric tip 30 has been shown and described, the present invention is not limited in this regard, as other tip configurations known to those skilled in the pertinent art can be substituted without departing from the broader aspects of the present invention. For example, an O-ring (not shown) can be positioned in a groove defined by the end 28 of the plunger 24 and sealingly engage the interior sleeve wall 16.

In addition, while a flexible hollow tube 22 has been described herein above, the present invention is not limited in this regard as the tube can be semi-flexible having an inherent rigidity or stiffness, such that it can be bent into and will retain a desired shape. This is useful when a patient is unable to open his or her mouth. In this situation, bending the tube to follow the contour of a patient's mouth between the teeth and cheek will facilitate easy insertion of the tube 22 into the patient's mouth. Moreover, the stiffness of the tube will allow the second end 32 to be slid far enough back in the patient's mouth to allow the patient to easily swallow the contents of the reservoir 15 as it is injected into the patient's mouth.

In operation, a second end 32 of the flexible hollow tube 22 is positioned in a receptacle containing the liquid, medication, or suspension. The receptacle can be of different types, such as a soft-drink can containing a nutritional supplement, a medicine vial, or simply a cup containing water. The contents of the receptacle are drawn through the hollow tube and into the reservoir 15, by manually moving the plunger from the first position adjacent to the closed second end 18 of the sleeve 12, to the second position adjacent to the open end 24 of the sleeve. The second end of the tube is then positioned in the patient's mouth and located near the entrance to the patient's throat. The contents of the reservoir 15 are then injected through the elongated hollow tube 22 into the patient's mouth by moving the plunger between the second and the first positions. The rate at which the contents of the reservoir 14 are injected into the patient's mouth is controlled by slowing or increasing the speed at which the plunger is moved between the second and the first positions.

A second embodiment of the apparatus of the present invention, shown in FIG. 2, is generally designated by the reference numeral 110. The apparatus 110 is similar in many respects to the apparatus 10 described above, and therefore like reference numerals preceded by the number 1 are used to indicate like elements. The apparatus 110 differs from the apparatus 10 in that a valve or stopcock 134 is interposed between the flange 120 extending from the closed second end 118 of the sleeve 112, and the elongated hollow tube 122. The stopcock 134 preferably includes a manual actuator, shown as a rotatable lever 136 in FIG. 2, that can be selectively operated to prevent or allow flow between the reservoir 114 and the elongated hollow tube 122.

As shown in FIG. 3, the stopcock 134 can also be adapted to be coupled to a second sleeve 138. In this manner, medication can be contained in the reservoir 114 of the first sleeve 112, and a nutritional supplement can be contained in the second sleeve 138. In operation, the lever 136 on the stopcock 134 can be turned to a first position to allow the medication in the first reservoir 114, but not the nutritional supplement contained in the second reservoir 140, to be injected into the patient's mouth. The lever 136 can then be turned to a second position to allow the contents of the second reservoir 140 to be injected into the patient's mouth.

While preferred embodiments have been shown and described, various modifications and substitutions may be made without departing from the spirit and scope of the present invention. Accordingly, it is to be understood that the present invention has been described by way of example, and not by limitation.

What is claimed is:

1. An apparatus for orally administering a dosage of a liquid, a suspension, or medication to patients able to swallow, but otherwise unable to independently ingest the liquid, medication, or suspension, comprising:

a sleeve for retaining the liquid, suspension, or medication, having at least one interior wall surface and a closed end, the closed end including an outwardly extending flange defining an aperture extending therethrough and in fluid communication with the interior of the sleeve;

a manually operable plunger having a stem portion, and an end adapted to slidingly and sealingly engage the interior wall surface to cooperatively define a reservoir with the sleeve interior wall surface an closed end, the plunger being movable between a first position wherein the end is adjacent to the closed end of the sleeve, and a second position wherein the end is adjacent to the opposite end of the sleeve;

an elongated hollow tube having a first end coupled to the flange and defining an aperture extending therethrough and in fluid communication with the reservoir;

a valve interposed between and coupled at one end to the flange and at an opposite end to the tube, the valve being manually operable between a closed position wherein the liquid, medication, or suspension retained in the reservoir of the sleeve, is prevented from leaking out of the tube and an open position wherein the liquid, medication, or suspension can be injected through the tube; and wherein the tube includes a second end adapted to be positioned at a point within a patient's mouth adjacent to the patient's throat, such that when the end of the plunger is moved from the second to the first position, the liquid, medication, or suspension contained within the reservoir of the sleeve is injected out of the second end of the tube and is readily swallowed by the patient.

2. An apparatus for orally administering a dosage of a liquid, a suspension, or medication as defined by claim 1, wherein at least a portion of the sleeve is transparent and defines indicia indicative of the amount of liquid, medication, or suspension present within the reservoir.

3. An apparatus for orally administering a dosage of a liquid, a suspension, or medication as defined by claim 1, wherein the tube is flexible.

4. An apparatus for orally administering a dosage of a liquid, a suspension, or medication as defined by claim 1, wherein the tube is semi-flexible and can be bent into a shape that facilitates the positioning of the tube at a desired location in the patient's mouth.

5. An apparatus for orally administering a dosage of a liquid, a suspension, or medication as defined by claim 1, wherein the sleeve is cylindrical.

6. An apparatus for orally administering a dosage of a liquid, a suspension, or medication as defined by claim 1, further comprising:

a stopcock interposed between, and coupled to the flange and the tube, the stopcock being adapted to be coupled to at least a second sleeve; and wherein the stopcock includes means enabling the contents of the respective reservoirs of each sleeve to be selectively injected through the tube and into the patient's mouth.

7. A method for orally administering a dosage of a liquid, a suspension, or medication to patients able to swallow, but otherwise unable to independently ingest the liquid, medication, or suspension, comprising the steps of:

providing an apparatus for orally administering a dosage of a liquid, a suspension, or medication that includes a sleeve for retaining the liquid, suspension, or medication, having at least one interior wall surface and a closed end, the closed end including an aperture extending therethrough and in fluid communication with the interior of the sleeve, a manually operable plunger having a stem portion, and an end adapted to slidingly and sealingly engage the interior wall surface to cooperatively define a reservoir with the sleeve interior wall surface and closed end, the plunger being movable between a first position wherein the end is adjacent to the closed end of the sleeve, and a second position wherein the end is adjacent to the opposite end of the sleeve, the plunger being movable between a first position wherein the end is adjacent to the second end of the sleeve, and a second position wherein the end is adjacent to the first end of the sleeve, a valve interposed between and coupled at one end to flange and being manually operable between a closed position wherein liquid medication or suspension retained in the reservoir sleeve is prevented from leaking, and an open position wherein the liquid, medication or suspension can be injected, and an elongated tube having a first end coupled to the valve and defining an aperture extending therethrough, in fluid communication with the reservoir, and wherein the tube includes a second end adapted to be positioned in a patient's mouth;

placing the second end of the tube into a receptacle containing the liquid, medication, or suspension;

operating the valve so that it is in the open position;

moving the plunger between the first and second positions, thereby drawing a predetermined amount of the liquid, medication, or suspension through the tube and into the reservoir of the sleeve;

operating the valve so that it is in the closed position;

positioning the second end of the tube at a desired location within the patient's mouth;

opening the valve; and injecting the contents of the reservoir into the patient's mouth by moving the plunger between the first and second positions.

8. The method of claim 7 wherein the tube is semi-flexible, and after the step of moving the plunger between the first and second positions, thereby drawing a predetermined amount of the liquid, medication, or suspension through the tube and into the reservoir of the sleeve; the method includes the further step of:

bending the tube to a configuration corresponding to the shape of the area between the teeth and cheek of a patient's mouth; and wherein the step of positioning the second end of the tube at a desired location within the patient's mouth includes inserting the tube into the patient's mouth such that the second end is located between the teeth and cheek of the patient adjacent to the patient's throat.

* * * * *

UNITED STATES PATENT AND TRADEMARK OFFICE

CERTIFICATE OF CORRECTION

PATENT NO. : 6,071,261
DATED : June 6, 2000
INVENTOR(S) : Augusto

It is certified that error appears in the above-identified patent and that said Letters Patent is hereby corrected as shown below:

Column 1,
Line 46: After "true with", delete "patient" and insert -- patients --.

Column 3,
Line 21: After "aperture", delete "22" and insert -- 19 --.
Line 25: After "the reservoir", delete "14' and insert -- 15 --.
Line 31: After "28 adapted", insert -- to --.
Line 41: After "the reservoir", delete "14" and insert -- 15 --.

column 4,
Line 6: After "open end", delete "24" and insert --14 --.
Line 12: After "the reservoir", delete "14" and insert -- 15 --.
Line 28: After "the reservoir", delete "114" and insert -- 115 --.
Line 31: After "the reservoir", delete "114" and insert -- 115 --.
Line 35: After "the first reservoir", delete "114" and insert -- 115 --.

Column 6,
Line 11: After "end to" insert -- the --.

Signed and Sealed this

Eighteenth Day of September, 2001

*Attest:*

Nicholas P. Godici

NICHOLAS P. GODICI

*Attesting Officer* *Acting Director of the United States Patent and Trademark Office*